United States Patent
Liverpool

(10) Patent No.: US 11,806,268 B2
(45) Date of Patent: Nov. 7, 2023

(54) SYSTEM FOR COLLECTING BODY WASTE OF NON-AMBULATORY PATIENTS

(71) Applicant: Thelma Rowena Liverpool, Bronx, NY (US)

(72) Inventor: Thelma Rowena Liverpool, Bronx, NY (US)

(*) Notice: Subject to any disclaimer, the term of this patent is extended or adjusted under 35 U.S.C. 154(b) by 631 days.

(21) Appl. No.: 16/947,393

(22) Filed: Jul. 30, 2020

(65) Prior Publication Data
US 2021/0015655 A1    Jan. 21, 2021

Related U.S. Application Data

(60) Provisional application No. 62/921,926, filed on Jul. 15, 2019.

(51) Int. Cl.
| *A61F 5/44* | (2006.01) |
| *A61G 7/02* | (2006.01) |
| *A61G 5/10* | (2006.01) |

(52) U.S. Cl.
CPC .......... *A61F 5/4407* (2013.01); *A61G 5/1002* (2013.01); *A61G 7/02* (2013.01)

(58) Field of Classification Search
CPC ........ A61F 5/4407; A61G 5/1002; A61G 7/02
See application file for complete search history.

(56) References Cited

U.S. PATENT DOCUMENTS

| 1,440,765 | A | * | 1/1923 | Buckley | A61F 5/44 4/144.1 |
| 2,483,612 | A | | 10/1949 | Beem | |
| 3,164,846 | A | * | 1/1965 | Foster | A61M 3/0208 4/420.1 |
| 3,668,720 | A | * | 6/1972 | Wetzler | A61G 7/02 5/604 |
| 3,678,932 | A | * | 7/1972 | Hudson | A61H 9/00 5/624 |
| 4,571,759 | A | * | 2/1986 | Sasaki | A61G 7/02 5/604 |
| 4,631,762 | A | * | 12/1986 | Fugett | A61G 7/02 5/605 |
| 4,677,700 | A | * | 7/1987 | Su | A61G 7/02 5/604 |
| 5,077,845 | A | * | 1/1992 | Tokunaga | A61G 7/02 5/652 |
| 5,331,689 | A | * | 7/1994 | Haq | A47K 11/12 604/326 |
| 5,461,738 | A | * | 10/1995 | Kimura | A61G 7/02 5/81.1 R |

(Continued)

*Primary Examiner* — Guy K Townsend
(74) *Attorney, Agent, or Firm* — Leason Ellis LLP

(57) ABSTRACT

A body waste collection system for bedridden or chair-bound patients. A waste entry port may interface with a resting surface of the bed or chair by way of a funnel that terminates at the resting surface. A collection unit may be fluidly coupled to the waste entry port by a flexible conduit system. The collection unit may include a temperature gauge, a volume measure, a sample port, and an odor removal port. Once the bedridden or chair-bound patient has assumed a release position along the resting surface defined by the waste entry port, no other lifting or movement of the patient is needed to collect their body waste in the collection unit, which can utilize the integrated hardware.

8 Claims, 4 Drawing Sheets

(56) References Cited

U.S. PATENT DOCUMENTS

| | | | |
|---|---|---|---|
| 5,513,404 A * | 5/1996 | Kanai | A61G 7/02 5/604 |
| 5,535,464 A * | 7/1996 | Salonica | A61G 7/02 5/942 |
| 5,604,943 A * | 2/1997 | Kimura | A61G 7/02 5/604 |
| 5,685,034 A * | 11/1997 | Kleer | A61G 7/02 5/604 |
| 5,729,849 A * | 3/1998 | Garakani | A61G 7/02 5/604 |
| 5,842,237 A * | 12/1998 | Hargest | A61G 7/012 5/605 |
| 5,848,443 A * | 12/1998 | Waugh | B60R 15/04 4/315 |
| 5,852,830 A * | 12/1998 | Horn | A47K 11/12 383/41 |
| 5,926,875 A * | 7/1999 | Okamoto | A61G 7/02 5/604 |
| 6,009,570 A * | 1/2000 | Hargest | A61G 7/012 5/604 |
| 6,101,646 A * | 8/2000 | Son | A61G 7/02 5/604 |
| 6,202,226 B1 * | 3/2001 | Shoptaugh | E03D 9/05 4/209 R |
| 6,684,414 B1 * | 2/2004 | Rehrig | A61G 9/006 4/144.1 |
| 6,725,474 B2 * | 4/2004 | Foster | A61G 7/0524 5/604 |
| 6,725,485 B2 * | 4/2004 | Hayes | A61G 7/02 5/604 |
| 6,740,066 B2 * | 5/2004 | Wolff | A61F 5/451 604/323 |
| 8,302,226 B2 * | 11/2012 | Hu | A61G 9/003 5/604 |
| 8,806,680 B2 * | 8/2014 | Ishida | A61G 7/02 5/604 |
| 10,316,503 B2 * | 6/2019 | Lu | A61G 9/00 |
| 2003/0181880 A1 * | 9/2003 | Schwartz | A61F 5/442 604/358 |
| 2003/0213065 A1 * | 11/2003 | Bristotti | A61G 7/05715 5/604 |
| 2004/6725485 | 4/2004 | Hayes | |
| 2007/0089227 A1 * | 4/2007 | Battiston | A61G 5/1002 4/480 |
| 2007/0240263 A1 * | 10/2007 | Kang | A61G 7/02 5/605 |
| 2008/0229502 A1 * | 9/2008 | Johnson | A61G 7/02 5/604 |
| 2008/0256708 A1 * | 10/2008 | Park | A61G 7/02 5/604 |
| 2010/0083441 A1 * | 4/2010 | Ishida | A61G 7/002 5/604 |
| 2010/0094233 A1 * | 4/2010 | Ashworth | A61F 5/4556 604/317 |
| 2010/0222754 A1 * | 9/2010 | Nishtala | A61F 5/4408 604/328 |
| 2011/0308017 A1 * | 12/2011 | Nakamura | A61G 9/00 5/605 |
| 2017/0020711 A1 * | 1/2017 | Nishtala | A61F 5/4408 |
| 2021/0015655 A1 * | 1/2021 | Liverpool | A61G 9/003 |

* cited by examiner

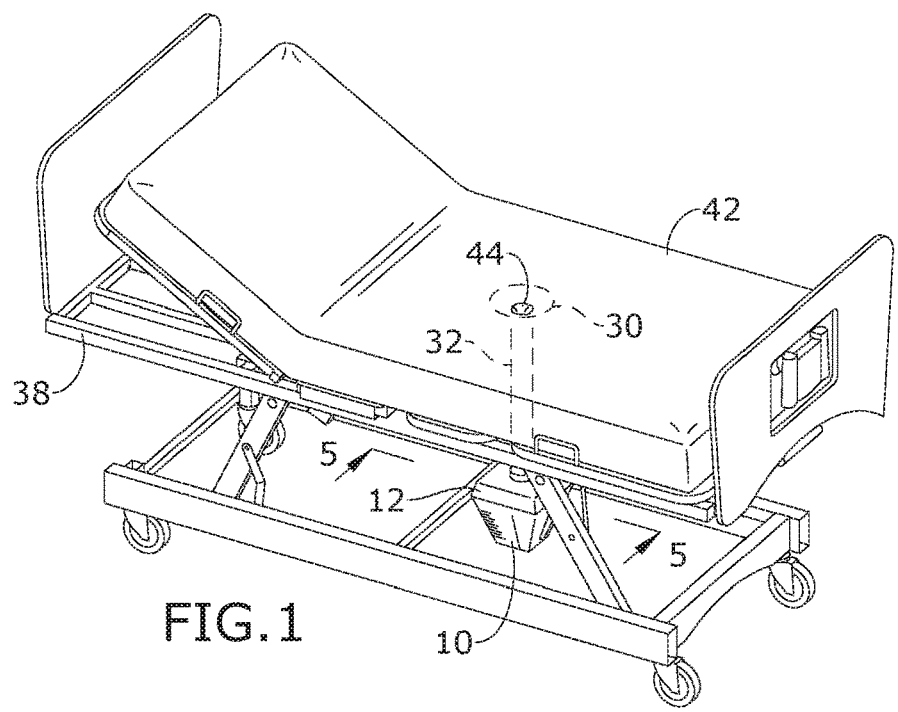
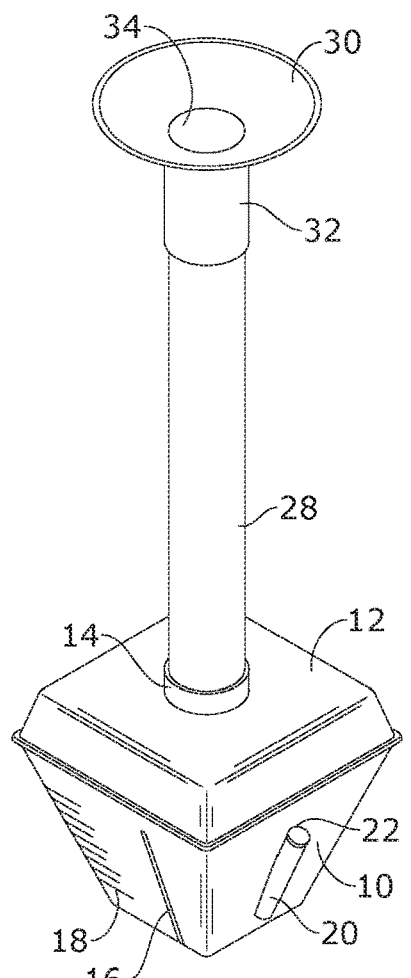
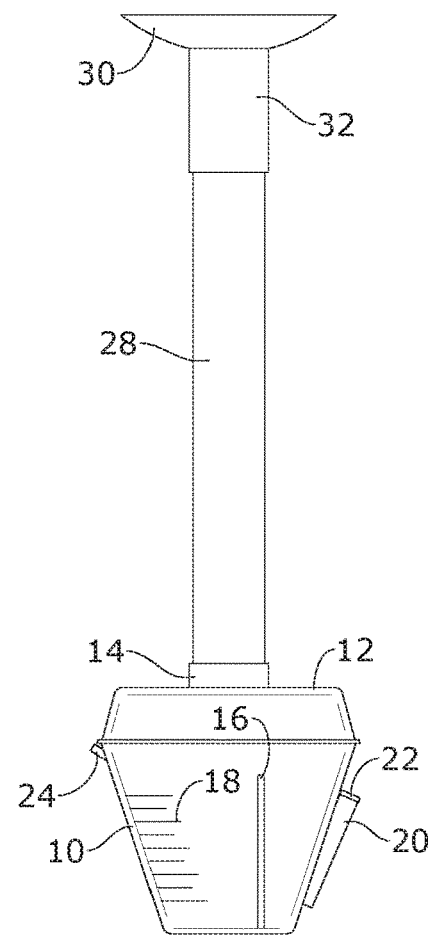
FIG.1
FIG.2
FIG.3

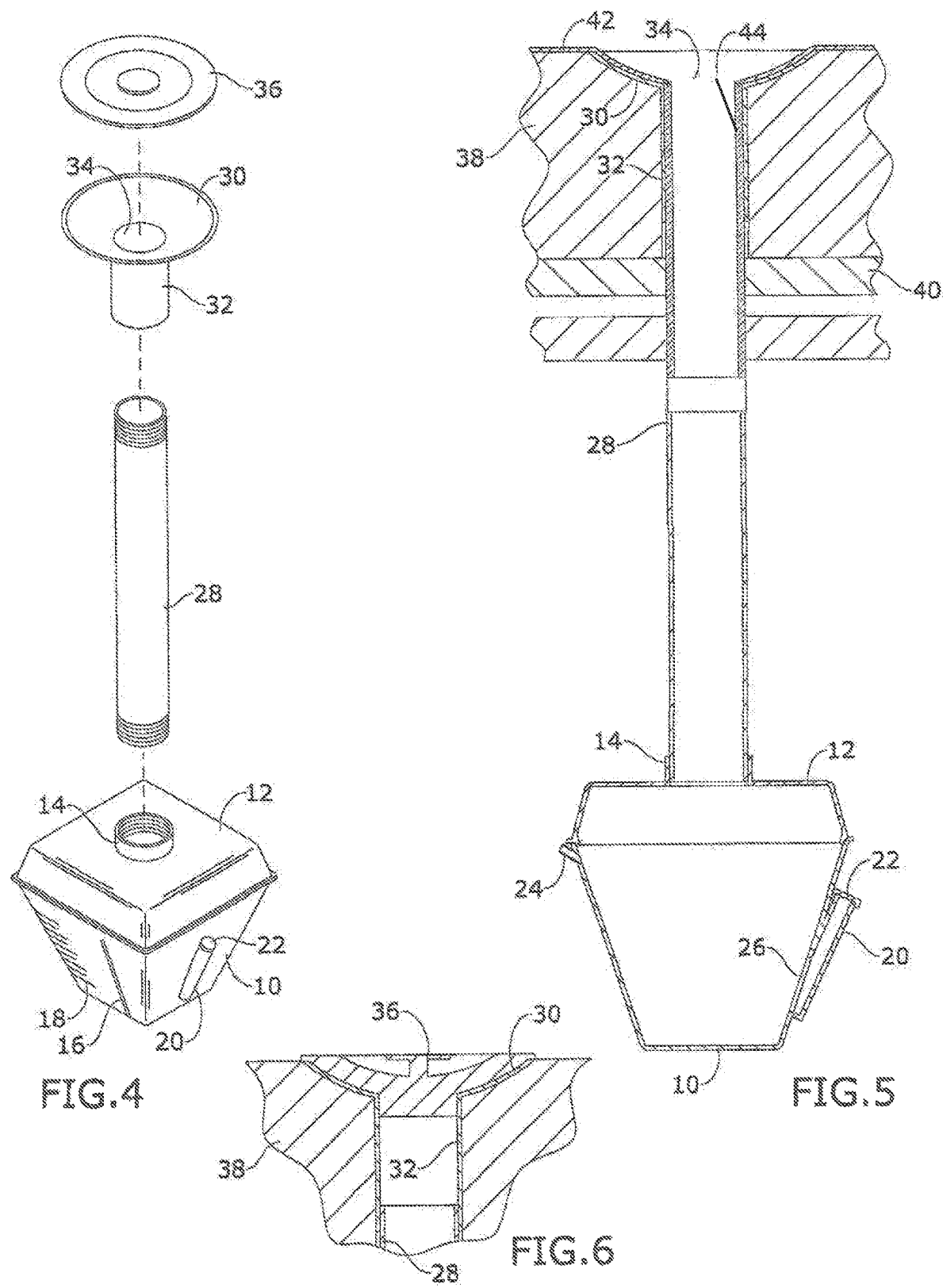

SYSTEM FOR COLLECTING BODY WASTE OF NON-AMBULATORY PATIENTS

CROSS-REFERENCE TO RELATED APPLICATION

This application claims the benefit of priority of U.S. provisional application No. 62/921,926, filed 15 Jul. 2019, the contents of which are herein incorporated by reference.

BACKGROUND OF THE INVENTION

The present invention relates to medical devices and, more particularly, a modification to beds and chairs in such a way so they are adapted to collect body waste from patients. The present invention embodies an attachment for modifying beds and chairs for collecting feces therefrom, thereby facilitating caring and cleaning for non-ambulatory patients.

To clean fecal matter of non-ambulatory patients, caregivers are required to lift the patient, which is problematic for the following reasons. First, such physical lifting can be hazardous to both parties: for example, back injuries to the caregiver. Also, the use of hoists is common and known to injure both the patient and attendant. Furthermore, among non-ambulatory patients an epidemic of obesity is well established, and so operation of hoists in lifting patients usually requires two caretakers. The patient is then undressed and bathed and the procedure reverses. In short, the overall process and the constituent parts of cleaning a non-ambulatory patient takes of the time and effort of the caregiver that could have been directed toward the patient in other endeavors.

Moreover, hazards to caregivers and medical personnel from handling infected waste is well known, from Ebola and other diseases.

Non-ambulatory patients develop bedsores and skin infections when improperly or insufficiently cleaned. For the elderly, in particular, these conditions can be life threatening.

Documented instances of neglect and abuse of bedridden patients almost always include the cessation of the changing of soiled undergarments and related cleaning of the non-ambulatory patient. And arguably this grueling, thankless task can play a role in the onset of said neglect and abuse. Also noteworthy, the number of adult diapers deposited to landfills is steadily increasing with an aging population. The environmental issues include groundwater contamination, as well as effects on birds and small animals who forage in these locations.

As can be seen, there is a need for a modification to beds and chairs in such a way that they are adapted to collect body waste from non-ambulatory patients. The modification enables the patient to be simply guided into a release position so that body waste is collected without physical touching of the patient—thereafter the patient is easily cleaned up and the overall experience is less traumatic for the patient.

As a result, the use of adult diapers is reduced, the patient will be more comfortable during the bowel movement process, there is minimum effort required of the caregiver except for cleanup, and the patient can also be washed or showered in place instead of being physically moved to a new location—which will reduce stress on the patient and the caregiver.

SUMMARY OF THE INVENTION

In one aspect of the present invention, a body waste collection system for a patient supported by a resting surface including the following: a waste entry port interfacing the resting surface; a collection unit fluidly coupled to the waste entry port by way of a flexible conduit system; and a sample port integrated to the collection unit. This also allows access to the waste for testing while providing an access point for reagents or sensors.

In another aspect of the present invention, the body waste collection system for a patient supported by a resting surface includes the following: a waste entry port interfacing the resting surface; a collection unit fluidly coupled to the waste entry port by way of a flexible conduit system; a sample port integrated to the collection unit; an air removal port integrated to the collection unit; a funnel extending upwardly from the waste entry port, wherein the funnel terminates at the resting surface, wherein a drain opening is formed through the resting surface; and a plug for sealing the waste entry port when not in use. This merges seamlessly with the surface of the bed for normal use.

In yet another aspect of the present invention a method of collecting a body waste from a bedridden patient, the method includes the following: providing the above-mentioned body waste collection system; positioning the bedridden patient in a release position along the non-permeable bedsheet defined by the waste entry port; and after collecting the body waste lifting distal edges of the bedsheet to assist a flow of the body waste through the waste entry port. This arrangement also allows for washing of the patient.

These and other features, aspects and advantages of the present invention will become better understood with reference to the following drawings, description and claims.

BRIEF DESCRIPTION OF THE DRAWINGS

FIG. 1 is a perspective view of an exemplary embodiment of the present invention, shown in an installed condition;

FIG. 2 is a perspective view of an exemplary embodiment of the present invention;

FIG. 3 is a side elevation view of an exemplary embodiment of the present invention;

FIG. 4 is an exploded perspective view of an exemplary embodiment of the present invention;

FIG. 5 is a section view of an exemplary embodiment of the present invention, taken along line 5-5 of FIG. 1;

FIG. 6 is a detailed view of a plugged waste entry port of an exemplary embodiment of the present invention;

DETAILED DESCRIPTION OF THE INVENTION

Figure 7:
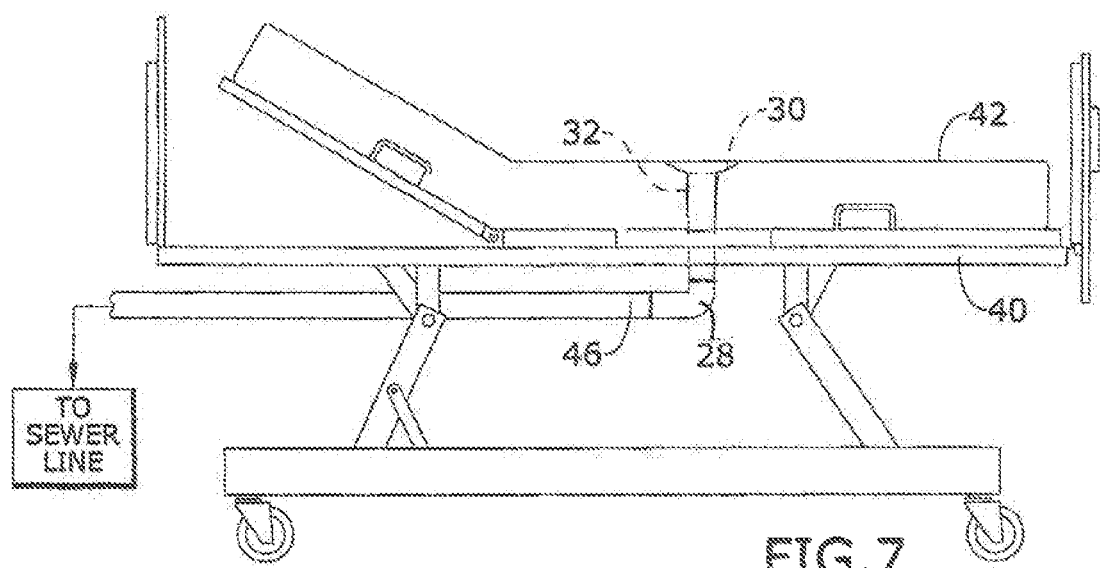
FIG. 7 is a side elevation view of an exemplary embodiment of the present invention.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a body waste collection system for bedridden or chair-bound patients. A waste entry port may interface with a resting surface of the bed or chair by way of a funnel that terminates at the resting surface. A collection unit may be fluidly coupled to the waste entry port by a flexible conduit system. The collection unit may include a temperature gauge, a volume measure, a sample port, and an air displacement port. Once the bedridden or chair-bound patient has assumed a release position along the resting surface defined by the waste entry port, no other lifting or movement of the patient is needed to collect their body waste in the collection unit, which can utilize the integrated hardware. At this point, samples of the waste can be removed via the sample port, or the entire collection unit can be removed by disengaging from the flexible unit. Reagents can be added directly to the container in order to give a desired reaction product to aid in analysis of the waste. The researcher is spared physical contact and possible infection from the waste. The waste is spared further contamination by being transferred to other containers.

The container gives visual information such as color, quantity, temperature, physical form [fluid or solid] which may be important to a caregiver. Flow rates can be easily calculated. The presence of sensors in the container may provide information which is transmitted electronically to a remote location or device. These are all parameters which assist in analyzing the state of health of a patient.

Referring now to FIGS. 1 through 11, the present invention may include a waste collection unit 10 that is fluidly connectable, by way of a flexible conduit system 28, 60, 70, to a waste entry port 34 or 58 in a resting surface, such as along a seat 68 of a chair 66 or the mattress 38 or 52 of a bed 62.

In certain embodiments, the flexible conduit system 60 may be oriented at transverse directions relative to the solid unit 56. A funnel 30 or 54 may extend upwardly from the waste entry port 34 or 58. A distal end of the funnel 30 or 54 may interface with the resting surface at a drain opening 44. The drain opening 44 may include an opening in a mattress 38, 52 and bed sheet 42 of the bed 62 or the seat 68 of the chair 66. In certain embodiments, the drain opening 44 could be a tubular element that is inserted into a rigid pipe 32. In other embodiments, the drain opening 44 could be a circular reinforcing, such as defining an opening in the bedsheet 42. Said interface may define a release position for anatomy of a patient discharging the body waste of fecal matter or urine. The waste entry port 34 or 58 may be closed off by a plug 36.

In other embodiments, the flexible conduit system may be 60 oriented at transverse directions relative to the rigid pipe 56. A funnel 30 or 54 may extend upwardly from the waste entry port 34 or 58. A distal end of the funnel 30 or 54 may interface with the resting surface or protrude slightly above or below the resting surface. The rigid pipe 32 may interconnect the flexible conduit system and the waste entry port 34 or 58 (in other words, the pipe 32 may be considered the solid portion of an overall conduit system). The rigid pipe 32 may extend entirely through the mattress 38 or 52; additionally, the rigid pipe 32 may also protrude through at least a portion below the frame 40. In certain embodiments, if a smaller patient is on the mattress 38 or 52, the rigid pipe 32 hardly moves; though, if a heavier patient has their mass bearing on the rigid pipe 32, it drops down more, and so the mattress 38 or 52 may squish, but the rigid pipe 32 just juts out more and remains solid. Since the rigid pipe 32 connects to the flexible conduit system (in FIG. 5, #28), no harm is done to the present invention because flexible conduit 28 would just bend under the force of the patient. When the patient gets up, the mattress 38 or 52 expands and the rigid pipe 32 moves back up.

The resting surface may be associate with a drain opening 44, which may be an opening in a mattress 38, 52 and bed sheet 42 of the bed 62 or the seat 68 of the chair 66. The above-mentioned interface may define a release position for anatomy of a patient discharging the body waste of fecal matter or urine. The waste entry port 34 or 58 may be closed off by a plug 36.

Figure 8:
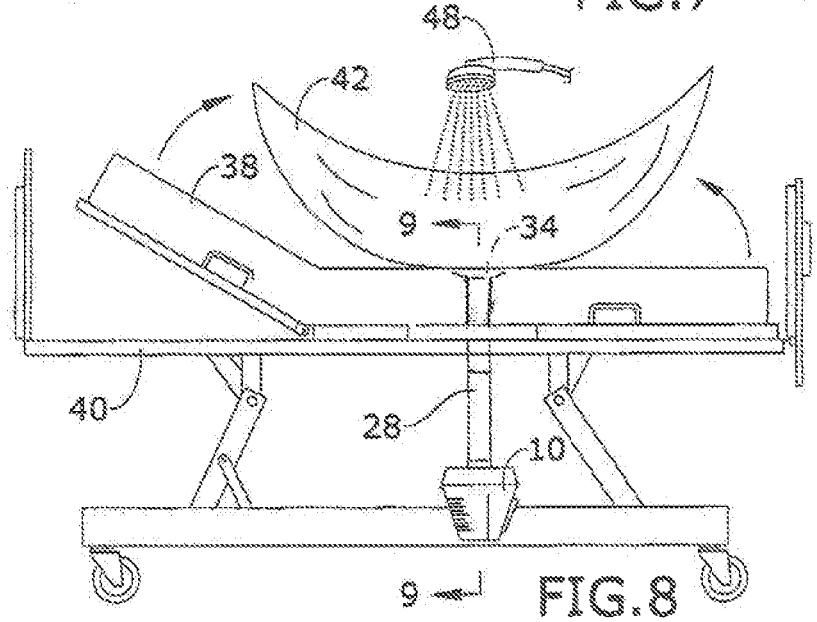
FIG. 8 is a side elevation view of an exemplary embodiment of the present invention, illustrating manipulation of sheet 42 to create flow into a waste entry port 34 or 58.
Figure 9:
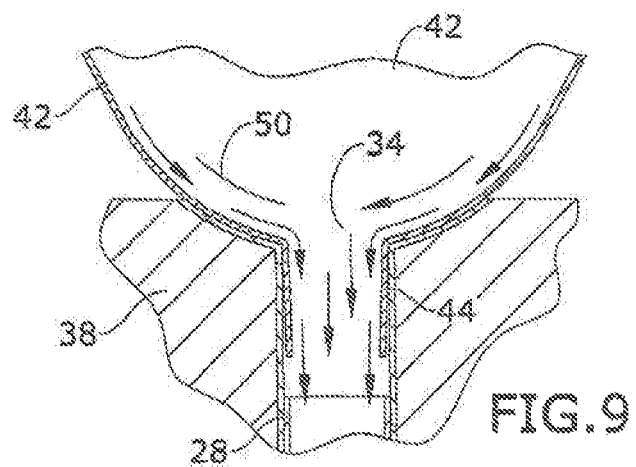
FIG. 9 is a detail section view of an exemplary embodiment of the present invention, taken along line 9-9 of FIG. 8.

In certain embodiments, the impermeable bedsheet 42 on the mattress 38, 52—having its own drain opening 44 to interface with the funnel 30 and thus the waste entry port 34 or 58—can be utilized as a makeshift funnel through lifting up the edges thereof, as illustrated in FIG. 8. In this embodiment, a water source 48 may be used to clean the impermeable bedsheet 42 and flush residual body waste down the waste entry port 24 by way of a flow 50.

The collection unit 10 has as its main opening the flange 14 coupling to the flexible conduit 28 or 70. The volume enclosed by the collection unit 10 is defined by sidewalls. The sidewalls may include a temperature gauge 16 and a volume measure 18. The sidewalls may also provide a sample port 20 with a sample port cap 22 for sealing the sample port 20. The sidewall may also house an air removal port 24.

In certain embodiments, the collection unit 10 can be removed and a sewer conduit 46 may fluidly connect to the flexible conduit 28.

In certain embodiments, a support pillow 64 may facilitate the patient assuming or being guided to the release position, similar to an adjustable hospital bed being moved to likewise assist the patient in assuming the release position. This would also occur when a normal bed is equipped with a portable version of the invention.

A method of using the present invention may include the following. The collection unit 10 disclosed above may be provided. The collection unit 10 may be fluidly coupled to the flexible conduit system 28, and 60, which in turn is fluidly connected to the waste entry port 34 or 58. The patient may be positioned over the drain opening 44 of the overall system disclosed above—at the release position. There the patient can release body waste without having to be moved off their bed or chair.

The collection unit 10 may be removed and the waste diverted to a sewer system—the flexible unit 28 is linked to the sewer line—when the waste is not infectious. The person can be cleaned by paper which is then flushed or a bidet-style cleaning by shower is possible. In certain embodiments, the flexible conduit system can be connected to the home waste-water system when substantial quantities of water are to be removed.

Figure 10:
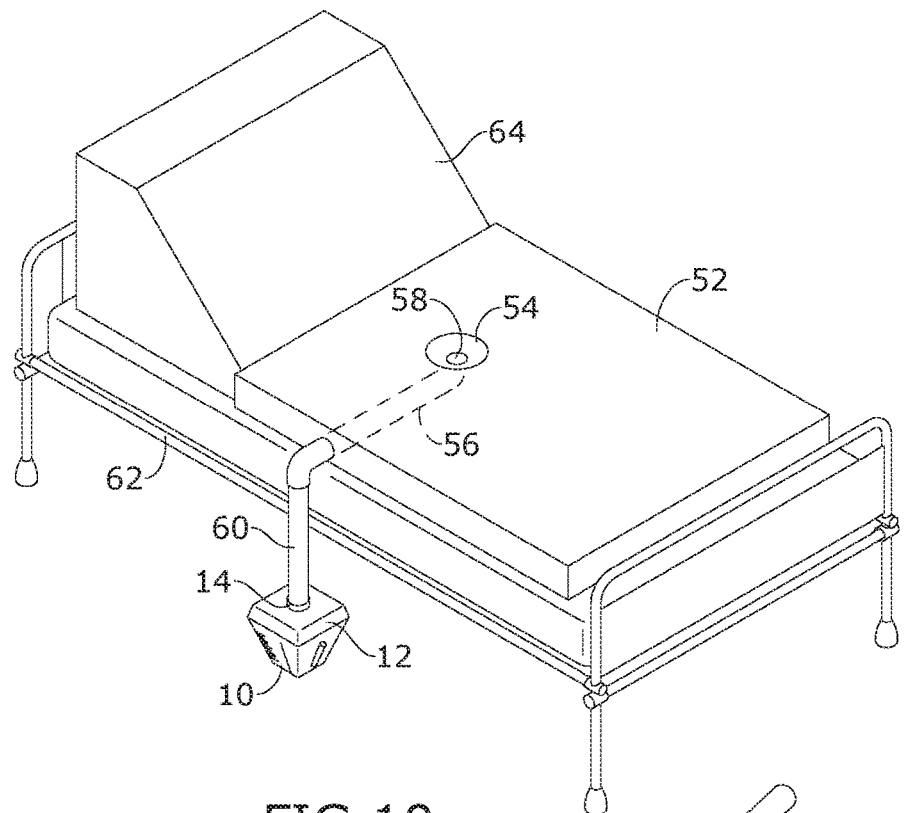
FIG. 10 is a perspective view of an exemplary embodiment of the present invention.
Figure 11:
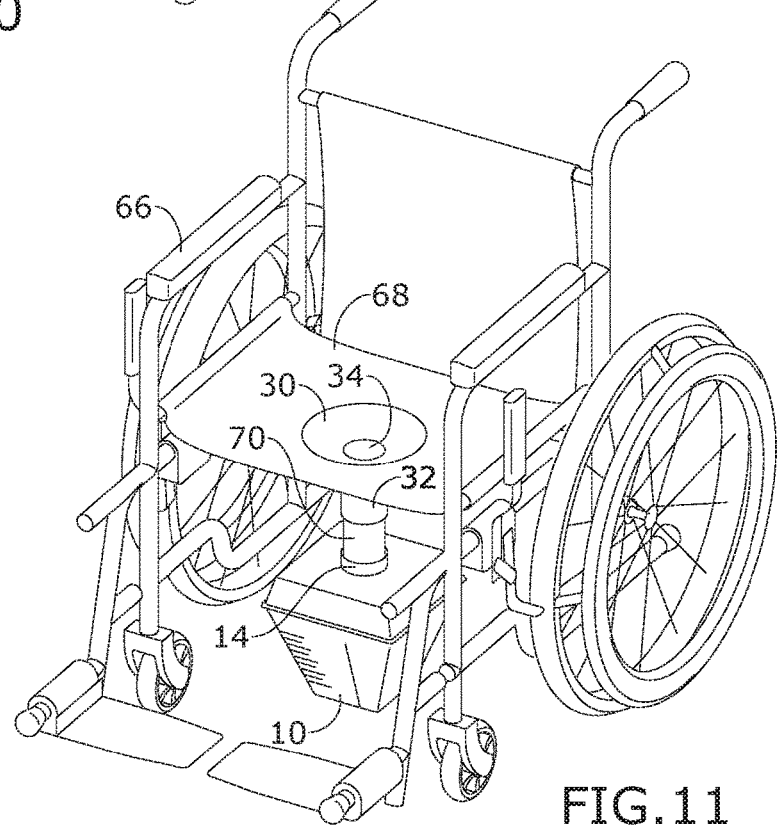
FIG. 11 is a perspective view of an exemplary embodiment of the present invention.

Additionally, the present invention can be made portable, allowing its use in transport vehicles. A portable unit can also be used at home if a bed should not be modified. This is shown in FIG. 10. The system can also be retrofitted onto wheelchairs per FIG. 11.

It should be understood, of course, that the foregoing relates to exemplary embodiments of the invention and that modifications may be made without departing from the spirit and scope of the invention as set forth in the following claims.

What is claimed is:

1. A body solid waste collection system for a patient supported by a resting surface, comprising:
   a solid waste entry port including a flange, interfacing the resting surface;
   a collection unit fluidly coupled to the waste entry port by way of a flexible conduit system and a rigid pipe, in which the collection unit, the flexible conduit system, and the rigid pipe are aligned collinearly, and each of the collection unit, the flexible conduit system, and the rigid pipe is respectively configured to have a uniform circumference throughout its length, thereby enabling passage of body solid waste from the entry port to the waste entry port; and
   a sample port integrated to the collection unit.

2. The body waste collection system of claim 1, further comprising a funnel extending upward from the waste entry port, wherein the funnel terminates at the resting surface.

3. The body waste collection system of claim 1, wherein a drain opening is formed through the resting surface.

4. The body waste collection system of claim 3, wherein the resting surface is a mattress of a bed.

5. The body waste collection system of claim 3, wherein the resting surface is a seat of a chair.

6. The body waste collection system of claim 4, wherein the resting surface further includes a bedsheet also having an associated drain opening.

7. The body waste collection system of claim 1, further comprising a plug for sealing the waste entry port.

8. A body waste collection system for a patient supported by a resting surface, comprising:
   a solid waste entry port interfacing the resting surface, the entry port having a flange;
   a collection unit fluidly coupled to a flexible conduit system;
   a rigid pipe fluidly connected to the flexible conduit system and the waste entry port, in which the collection unit, the flexible conduit system, and the rigid pipe are aligned collinearly, and each of the collection unit, the flexible conduit system, and the rigid pipe is respectively configured to have a uniform circumference throughout its length, thereby enabling passage of body solid waste from the entry port to the waste entry port;
   a sample port integrated to the collection unit;
   an odor removal port integrated to the collection unit;
   a funnel extending upwardly from the waste entry port, wherein the funnel terminates at the resting surface, wherein a drain opening is formed through the resting surface; and
   a plug for sealing the waste entry port.

* * * * *